(12) United States Patent
Jia

(10) Patent No.: US 6,767,955 B2
(45) Date of Patent: Jul. 27, 2004

(54) FLOWABLE DENTAL RESIN MATERIALS AND METHOD OF USE THEREOF

(75) Inventor: Weitao Jia, Wallingford, CT (US)

(73) Assignee: Pentron Clinical Technologies, Wallingford, CT (US)

( * ) Notice: Subject to any disclaimer, the term of this patent is extended or adjusted under 35 U.S.C. 154(b) by 27 days.

(21) Appl. No.: 10/141,490

(22) Filed: May 8, 2002

(65) Prior Publication Data

US 2003/0212194 A1 Nov. 13, 2003

(51) Int. Cl.⁷ .............................................. C08F 216/04
(52) U.S. Cl. ........................ 524/556; 524/494; 524/537; 525/374; 523/115; 523/116; 523/117; 528/196; 528/106
(58) Field of Search ................................ 524/556, 494, 524/537; 525/374; 523/115, 116, 117; 528/196, 106

(56) References Cited

U.S. PATENT DOCUMENTS

| | | | |
|---|---|---|---|
| 3,066,112 A | 11/1962 | Bowen | 260/41 |
| 3,179,623 A | 4/1965 | Bowen | 260/47 |
| 3,194,784 A | 7/1965 | Bowen | 260/41 |
| 3,751,399 A | 8/1973 | Lee, Jr. et al. | 260/47 |
| 3,926,906 A | 12/1975 | Lee, II et al. | 260/42.53 |
| 4,472,141 A | 9/1984 | Dragan | |
| 4,544,349 A | 10/1985 | Nakamura et al. | 431/258 |
| 4,547,531 A | 10/1985 | Waknine | 523/116 |
| 4,601,662 A | 7/1986 | Galler | |
| 4,616,073 A | 10/1986 | Antonucci | 526/246 |
| 4,648,843 A | 3/1987 | Mitra | |
| 4,696,955 A | 9/1987 | Kuhlmann | |
| 4,957,441 A | 9/1990 | Bryan | |
| 4,964,911 A | 10/1990 | Ibsen et al. | |
| 5,154,762 A | 10/1992 | Mitra et al. | 106/35 |
| 5,228,907 A | 7/1993 | Eppinger et al. | |
| 5,246,371 A | 9/1993 | Fischer | |
| 5,276,068 A | 1/1994 | Waknine | 522/28 |
| 5,308,886 A | 5/1994 | Masuhara et al. | |
| 5,334,625 A | 8/1994 | Ibsen et al. | |
| 5,336,088 A | 8/1994 | Discko, Jr. | |
| 5,378,737 A | 1/1995 | Jacobs et al. | |
| 5,425,641 A | 6/1995 | Fischer | |
| 5,444,104 A | 8/1995 | Waknine | |
| 5,460,523 A | 10/1995 | Schulman | |
| 5,472,991 A | 12/1995 | Schmitt et al. | |
| 5,547,379 A | 8/1996 | Hasel | |
| 5,621,119 A | 4/1997 | Podszun et al. | |
| 5,684,103 A | 11/1997 | Jia et al. | 526/218.1 |
| 5,861,445 A | 1/1999 | Xu et al. | 523/116 |
| 5,944,527 A | 8/1999 | Hasel | |
| 5,969,000 A | 10/1999 | Yang et al. | 523/116 |
| 6,013,694 A * | 1/2000 | Jia et al. | 523/116 |
| 6,030,606 A | 2/2000 | Holmes | 424/49 |

* cited by examiner

Primary Examiner—David W. Wu
Assistant Examiner—Satya Sastri
(74) Attorney, Agent, or Firm—Cantor Colburn LLP

(57) ABSTRACT

A dental restorative composition comprises about 35 to about 43 wt %, based on the total dental restorative composition, of a polymerizable, ethylenically unsaturated resin composition, wherein the resin composition comprises, based on the resin composition alone, about 25 to about 35 wt % PCDMA, about 40 to about 50 wt % EBP-DMA, about 18 to about 28 wt % Bis-GMA, and about 55 to about 70 wt %, based on the total dental restorative composition, of a filler system, wherein the filler system comprises a silanized barium glass containing about 20 to about 60 wt % barium oxide based on the weight of silanized barium glass. Such dental restorative compositions display an ability to flow under ambient conditions and this increases their utility where improved flexural strength and ease of application is desired.

15 Claims, No Drawings

FLOWABLE DENTAL RESIN MATERIALS AND METHOD OF USE THEREOF

BACKGROUND

1. Field of the Invention

This disclosure relates to filled, flowable, light polymerizable polymeric compositions useful in restorative dentistry. Flowable, filled compositions can be used as crown and bridge materials either with or without alloy substrates; as reconstructive materials, filling materials, inlays, onlays, laminate veneers and the like, as luting agents or cements, and as orthodontic materials, sealants and the like.

2. Brief Description of the Related Art

In recent years, materials used for restorative dentistry have comprised principally acrylic resin systems, that is, acrylate or methacrylate polymers. Typical acrylate resinous materials are disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al. and U.S. Pat. No. 3,926,906 to Lee et al. Because acrylic resins alone are less than satisfactory, composite dental restorative materials containing resins and fillers were developed. The fillers are generally inorganic materials based on silica, silicate based glasses, or quartz.

Over the years, there have been a number of refinements in the matrix resins, fillers and other additives such as antioxidants, ultraviolet absorbers, polymerization initiators, polymerization accelerators, and the like, used in dental restorative materials. There are now available materials which exhibit high diametral tensile strength, excellent optical properties and polishability, and low water absorption while, at the same time, complying with all of the requirements specified in the American Dental Association (ADA) Specification No. 27 for direct filling resins. Particularly suitable dental restorative materials are compositions having improved inorganic filler materials such as those described in U.S. Pat. Nos. 4,547,531 and 4,544,359, disclosing visible light polymerizable compositions.

Despite recent advances in the development of filled dental restorative materials there remain opportunities for improvement in the flexural strength of composites used as crown and bridge materials, denture base materials, luting agents or cements, orthodontic appliance materials and sealants. In particular, improving the handling characteristics of dental restorative materials that facilitates ease of application is highly desirable.

BRIEF SUMMARY

A dental restorative composition comprises about 35 to about 43 wt %, based on the total dental restorative composition, of a polymerizable, ethylenically unsaturated resin composition, wherein the resin composition comprises, based on the resin composition alone, about 25 to about 35 wt % PCDMA, about 40 to about 50 wt % EBP-DMA, about 18 to about 28 wt % Bis-GMA, and about 55 to about 70 wt %, based on the total dental restorative composition, of a filler system, wherein the filler system comprises a silanized barium glass containing about 20 to about 60 wt % barium oxide based on the weight of silanized barium glass.

DETAILED DESCRIPTION OF THE PREFERRED EMBODIMENTS

It has been unexpectedly discovered that a dental restorative composition comprising polymerizable, ethylenically unsaturated resins such as polycarbonate dimethacrylate (PCDMA), 2,2'-bis [4-(3-methacryloxy-2-hydroxy propoxy)-phenyl]-propane (hereinafter abbreviated "Bis-GMA") and ethoxylated bisphenol A dimethacrylate (EBP-DMA) in the proportions specified above and an effective concentration of silanized barium glass fillers, possesses unique Theological characteristics which renders it flowable at ambient temperatures and pressures. This ability to flow at ambient conditions, combined with superior flexural strength, ability to undergo curing with visible light and appropriate shelf life make the dental restorative composition very useful in applications where ease of applicability and long life in an oral cavity are desired.

The PCDMA, typically produced as the result of a reaction between two parts hydroxyalkylmethacrylate and one part of a bis(chloroformate) is detailed in U.S. Pat. Nos. 5,276,068 and 5,444,104 to Waknine, both of which are incorporated herein by reference, is present in an amount greater than or equal to about 25, preferably greater than or equal to about 29 (weight percent) wt % of the total resin composition. In general it is desirable to have the PCDMA present in an amount of less than or equal to about 35, preferably less than or equal to about 33 wt % of the total resin composition.

Bis-GMA is the condensation product of bisphenol A and glycidyl methacrylate and is generally present in an amount greater than or equal to about 18, preferably greater than or equal to about 20 wt % of the total resin composition. It is desirable to have the Bis-GMA present in an amount less than or equal to about 27, preferably less than or equal to about 25 wt % of the total resin composition.

The EBP-DMA is present in an amount greater than or equal to about 40, preferably greater than or equal to about 43 wt % of the total resin composition. It is generally desirable to have the EBP-DMA present in an amount less than or equal to about 50, preferably less than or equal to about 47 wt % of the total resin composition. Suitable examples of EBP-DMA that can be used in the preparation of the dental restorative composition are commercially available from Sartomer under the trade name SR348 and SR480.

It is generally desirable to have the polymerizable, ethylenically unsaturated resin present in an amount greater than or equal to about 35, preferably greater than or equal to about 37 wt % of the total dental restorative composition. In general it is desirable to have the polymerizable, ethylenically unsaturated resin present in an amount of less than or equal to about 43 wt %, preferably less than or equal to about 41 wt % of the total dental restorative composition.

In addition to the polymerizable, ethylenically unsaturated resin, the resin compositions can optionally include a diluent acrylate or methacrylate monomer to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate and tetra(ethylene glycol)dimethacrylate; and diol dimethacrylates such as butanedimethacrylate, dodecanedimethacryalte, or 1,6-hexanedioldimethacrylate. Tri(ethylene glycol)dimethacrylate (TEGDMA) is particularly preferred. Diluent monomers, when present, are incorporated into the resin composition in an amount of less than or equal to about 10 wt % of the total resin composition.

The filler system, which comprises silanized barium glass is generally present an amount effective to enhance flexural strength while maintaining the flowability of the dental restorative composition. Silanization refers to treating the surface of the fillers with a thin film of reactive siloxane, one end of which bonds to the filler, while the other end bonds to the matrix. The silanized barium glass generally comprises barium oxide in an amount of greater than or equal to about 20, preferably greater than or equal to about 30, more preferably greater than or equal to about 35 wt % of the total weight of the silanized barium glass. It is desirable to have the barium oxide in an amount of less than or equal to about 60, preferably less than or equal to about 50, more preferably less than or equal to about 45 wt % of the total weight of the silanized barium glass. Use of these quantities of barium oxide results in enhanced radiopacity.

The silanized barium glass is particulate (either irregular, e.g., acicular, rod like, or regular, e.g., spherical), and preferably has average dimensions (particle sizes) greater than or equal to about 0.01, preferably greater than or equal to about 0.1, more preferably greater than or equal to about 0.3 microns. It is generally desirable to have the average particle dimensions less than or equal to about 10, preferably less than or equal to about 5, more preferably less than or equal to about 2 microns. Suitable glasses are commercially available from, for example, Ferro Corporation, Cleveland, Ohio.

The silanized barium glass is generally present in an amount greater than or equal to about 55, preferably greater than or equal to about 57 wt % of the total dental restorative composition. It is also desirable to have the silanized barium glass present in an amount less than or equal to about 70, preferably less than or equal to about 68 wt % of the total dental restorative composition.

In addition to the silanized barium glass, commercially available, synthetic, fumed, or colloidal silicas may be used for viscosity adjustment and improved handling characteristics. Such silicas have an average particle size of about 0.001 to about 0.07 microns, and are preferably silanized with a silane-coupling agent such as γ-methacryloyloxypropyltrimethoxysilane. Un-silanized fillers can also be incorporated into the dental restorative compositions. Examples of suitable silicas are the "Aerosil" series OX-50, OX-130, and OX-200 silica sold by Degussa, and "Cab-O-Sil M5" and "Cab-O-Sil TS-530" silica sold by Cabot Corp.

Other surface reactive glasses such as aluminosilicate glass powders may also be used in the filler system. In particular, fluoroaluminosilicate glass powders having particle sizes of about 0.2 to about 10 microns, capable of releasing a fluorine ion, and comprising about 20 to about 50 wt % of silica, about 20 to about 40 wt % of alumina ($Al_2O_3$), about 15 to about 40 wt % of strontium oxide (SrO), and about 1 to about 20 wt % of fluorine ($F_2$), as described in Published Japanese Patent Application No. 55882/1995 can be suitably used. The reactive glass powder can contain a lanthanide metal element such as La, Gd, or Yb, if desired. When such fluoroaluminosilicate glass powder is contained in a dental restorative composition it exhibits an ability to release a fluorine ion.

In addition to the fluoroaluminosilicate glasses mentioned above, the filler system may also comprise one or more of the inorganic fillers currently used in dental restorative materials. Examples of suitable inorganic fillers include but are not limited to silica, quartz, strontium silicate, strontium borosilicate, lithium silicate, lithium alumina silicate, amorphous silica, ammoniated or deammoniated calcium phosphate, alumina, zirconia, tin oxide, and titania. Some of the aforementioned inorganic filling materials and methods of preparation are disclosed in U.S. Pat. Nos. 4,544,359 and 4,547,531, pertinent portions of which are incorporated herein by reference. Calcium phosphates are generally preferred, for example, calcium phosphates and tricalcium phosphate. Certain radiopaque/high refractive index materials may be used as filler materials. Suitable high refractive index filler materials include, but are not limited to, high refractive index silica glass fillers; calcium based fillers such as apatites, hydroxyapatites or modified hydroxyapatite compositions. Alternatively, inert, non-toxic radiopaque materials such as bismuth oxide ($Bi_2O_3$), barium sulfate, and bismuth subcarbonate may also be used.

The synthetic, fumed or colloidal silica fillers, fluoroaluminosilicate glasses or other inorganic fillers, or combinations thereof are optional and may generally be utilized in an amount greater than or equal to about 0, preferably greater than or equal to about 1 wt % of the total dental restorative composition and generally utilized in amounts of less than or equal to about 4, preferably less than or equal to about 3 wt % of the total dental restorative composition.

In addition to the above monomers and oligomers, the dental restorative materials also typically contain curing systems and other additives, e.g., polymerization initiators, polymerization accelerators, ultraviolet light absorbers, antioxidants, and other additives well known in the art. Suitable polymerization initiators are those conventional initiators well known in the art. For example, visible light polymerizable compositions employ light-sensitive compounds, including but not being limited to benzil, benzoin, benzoin methyl ether, DL-camphorquinone (CQ), and benzil diketones. Either UV-activated cure or visible light-activated cure (approximately 230 to 750 nm) can be used. The amount of photoinitiator is selected according to the cure rate desired. A minimal catalytically effective amount is generally about 0.01 wt % of the total resin composition, and will lead to a slower cure. Faster rates of cure are achieved with catalyst amounts of about 0.01 to about 5 wt % of the total resin composition. Alternatively, the composition may be formulated as a self-curing system. Self-curing compositions will generally contain free radical polymerization initiators such as, for example, a peroxide in amounts of about 0.05 to about 3.0 wt % of the total resin composition. Particularly suitable free radical initiators are lauryl peroxide, tributyl hydroperoxide and, more particularly benzoyl peroxide. It is preferred to employ light-sensitive compounds so that visible light can be used to cure the dental restorative composition.

Polymerization accelerators suitable for use are the various organic tertiary amines well known in the art. In visible light polymerizable compositions, the tertiary amines are generally acrylate derivatives such as dimethylaminoethyl methacrylate and, particularly, diethylaminoethyl methacrylate (DEAEMA) in amounts of about 0.05 to about 0.5 wt % of the total resin composition. In self-curing compositions, the tertiary amines are generally aromatic tertiary amines, preferably tertiary aromatic amines such as ethyl 4-(dimethylamino)benzoate (commonly known as "EDMAB"), 2-[4-(dimethylamino)phenyl]ethanol, N,N-dimethyl-p-toluidine (commonly abbreviated "DMPT"), bis(hydroxyethyl)-p-toluidine, and triethanolamine and are generally present in amounts of about 0.5 to about 4.0 wt % based on the resin composition.

Ultraviolet light absorbers are particularly desirable in the visible light polymerizable compositions in order to avoid discoloration of the resin from any incident ultraviolet light. Suitable ultraviolet light absorbers are the various benzophenones, particularly UV-5411 available from American Cyanamid Company and benzotriazoles known in the art, particularly 2-(2'-hydroxy-5'-methylphenyl)-benzotriazole, sold under the trademark TINUVIN P by Ciba-Geigy Corporation, Ardsley, N.Y. It is furthermore preferred to employ an ultraviolet absorber in amounts of about 0.05 to about 5.0 wt % based on resin composition.

The above-mentioned components i.e., the polymerizable, ethylenically unsaturated resin comprising PCDMA, Bis-GMA, and EBP-DMA, silanized barium glasses, synthetic or colloidal silica fillers, polymerization initiators and accelerators may be provided to the practioner as a one-part or two-part system. In the one-part system, the curing reaction may be triggered shortly before usage in dental restorative applications by the utilization of visible light, UV light or increased temperature. This one-opart flowable composition comprising the resin, filler system and curing system has a viscosity greater than or equal to about 200 Pascal-seconds (Pa-s), preferably greater than or equal to about 300 Pa-s, more preferably greater than or equal to about 450 Pa-s. It is desirable to have the viscosity of the single flowable composition less than or equal to about 800 Pa-s, preferably less than or equal to about 700 Pa-s, more preferably less than or equal to about 650 Pa-s at room temperature and atmospheric pressure.

Optionally, the various components forming the dental restorative composition may be divided into two parts, with a first part comprising, for example, a portion of the polymerizable, ethylenically unsaturated resin comprising PCDMA, Bis-GMA, and EBP-DMA, silanized barium glasses, and synthetic or colloidal silica fillers, and the second part containing the remaining portion of the polymerizable, ethylenically unsaturated resin along with other reactive glasses and fillers, polymerization initiators, accelerators, and the like. When a two-part system is used as a dental restorative, the two parts are mixed thoroughly before use. After mixing of the two parts, the composition has a viscosity greater than or equal to about 200 Pascal-seconds, preferably greater than or equal to about 300 Pa-s, more preferably greater than or equal to about 450 Pa-s. It is desirable to have the viscosity less than or equal to about 800 Pa-s, preferably less than or equal to about 700 Pa-s, more preferably less than or equal to about 650 Pa-s at room temperature and atmospheric pressure. The two part system may employ self-curing or light curing or both if desirable.

Dental restoratives made in such a manner display good aesthetics, easy handling, improved radiopacity, improved mechanical properties such as strength and wear resistance. As a result, longer-lasting restorations can be obtained with applications being extended to areas of the oral cavity subjected to moderate to high stresses. In addition, this composition displays an ability to self level when dispensed through a 20-gauge tip, which facilitates ease of handling in dental applications.

The various embodiments of this disclosure are further illustrated by the following non-limiting examples.

Two flowable dental restorative compositions were prepared comprising the resin formulations shown in Table 1 below, wherein amounts are given in weight percent of the total composition:

TABLE 1

| Components | Sample A | Sample B* |
|---|---|---|
| Bis-GMA | 22.65 | 12.74 |
| EBP-DMA | 44.31 | 42.62 |
| PCDMA | 31.51 | — |
| TEGDMA | — | 42.62 |
| Camphorquinone | 0.10 | 0.20 |
| EDMAB | 0.20 | 0.59 |
| Lucirin TPO | 0.49 | |
| UV-5411 | 0.73 | 0.73 |
| BHT | — | 0.005 |
| Tinuvin 292 | — | 0.49 |
| Uvitex OB | 0.01 | 0.01 |
| LUMILUX Blue LZ | 0.02 | — |

*Comparative Sample

In Table 1, Sample A comprises Bis-GMA, EBP-DMA and PCDMA as the polymerizable, ethylenically unsaturated resins, while Sample B contains Bis-GMA, EBP-DMA and tri(ethylene glycol dimethacrylate) (TEGDMA). Camphorquinone or Lucirin TPO is used as the polymerization initiator, and UV-5411 is the ultraviolet absorber. EDMAB (ethyl 4-(dimethylamino)benzoate) is used to promote the light curing and LAMILUX Blue LZ, is used for color adjustment of the dental restorative composition BHT is used as an antioxidant, Tinuvin 292 is used as a light stabilizer and Uvitex OB is used as a whitening agent.

Samples A and B were each produced by mixing the components shown in Table 1 followed by mixing with a filler system comprising silane treated barium borosilicate glass (Schott Glass, average particle size 0.7 microns, comprising about 40 weight percent of barium oxide) and silica (Cab-O-Sil T530, Cabot Corp.). The final flowable dental restorative composition comprised 38 wt % resin system, 60 wt % barium glass, and 2 wt % silica, based on the total weight of the dental restorative composition. Sample B was produced similarly. The final dental restorative composition comprised 32 wt % of the resin system, 66 wt % silane treated barium borosilicate glass (Schott Glass, comprising about 30 weight percent of barium oxide), and 2 wt % silica (Cab-O-Sil T530, Cabot Corp.

In the Table 2 it can be seen that Sample A in accordance with the present invention has superior flexural strength (greater than 18,000 psi) as compared with Sample B and other commercially available dental restorative compositions.

TABLE 2

| Flowable Composite (Shade) | Manufacturer and Batch Number | Flexural Strength, psi (S.D.)** |
|---|---|---|
| Sample A | Jeneric/Pentron, 32969 | 19646 (1709) |
| Revolution Formula 2 (A2)* | Kerr, 908B53 | 13925 (652)+ |
| Sample B* | Jeneric/Pentron, 25726 | 15451 (1144)+ |
| Aelite Flo (A2)* | BisCo, 07957 | 15345 (967)+ |
| Appollo Flo (A2)* | DMD, 18909 | 14380 (884)+ |
| Heliomolar Flow (A3)* | Vivadent, B08340 | 12872 (814)+ |
| Sinfony DD4* | ESPE, 005 | 13544 (953)+ |

*Comparative
**(S.D.) = Standard deviation

While preferred embodiments have been shown and described, various modifications and substitutions may be made thereto without departing form the spirit and scope of the invention. Accordingly, it is to be understood that the present invention has been described by way of illustration and not limitation.

What is claimed is:

1. A dental restorative composition comprising:
about 35 to about 43 wt %, based on the total dental restorative composition, of a polymerizable, ethylenically unsaturated resin composition, wherein the resin composition comprises, based on the resin composition,
about 25 to about 35 wt % PCDMA;
about 40 to 50 wt % EBP-DMA;
about 18 to about 28 wt % Bis-GMA;
about 55 to about 65 wt %, based on the total dental restorative composition, of a filler system, wherein the filler system comprises a silanized barium glass containing about 20 to about 60 wt % barium oxide based on the barium glass; and
a curing system.

2. The composition of claim 1, wherein the polymerizable, ethylenically unsaturated component comprises about 37 to about 41 wt % of the total dental restorative composition.

3. The composition of claim 1, wherein the barium glass comprises about 57 to about 63 wt % of the total dental restorative composition.

4. The composition of claim 1, wherein the barium glass comprises about 30 to about 50 wt % barium oxide, based on the total weight of the silanized barium glass.

5. The composition of claim 1, wherein the barium glass comprises about 35 to about 45 wt % barium oxide based on the total weight of the silanized barium glass.

6. The composition of claim 1, wherein the barium glass comprises particles having an average particle size of about 0.01 to about 10 microns.

7. The composition of claim 1, wherein the barium glass comprises particles having an average particle size of about 0.1 to about 5 microns.

8. The composition of claim 1, wherein the barium glass comprises particles having an average particle size of about 0.3 to about 2 microns.

9. The composition of claim 1, wherein the dental restorative composition comprises a single flowable component, with a viscosity of about 200 Pa-s to about 800 Pa-s.

10. The composition of claim 1, wherein the dental restorative composition further comprises an optional filler selected from the group consisting of fumed silica, colloidal silica, aluminosilicate glass, fluoroaluminosilicate glass, silica, quartz, strontium silicate, strontium borosilicate, lithium silicate, lithium alumina silicate, amorphous silica, ammoniated or deammoniated calcium phosphate, alumina, zirconia, tin oxide, titania, and combinations comprising at least one of the foregoing fillers and wherein the optional filler if present, comprises an amount of less than or equal to about 4 wt % of the total dental restorative composition.

11. A method of forming a dental restoration, comprising:
applying the composition of claim 1 to a tooth to be restored; and
curing the composition.

12. A dental restorative composition comprising:
about 35 to about 43 wt %, based on the total dental restorative composition, of a polymerizable, ethylenically unsaturated resin composition, wherein the resin composition comprises, based on the resin composition alone,
about 25 to about 35 wt % PCDMA;
about 40 to 50 wt % EBP-DMA;
about 18 to about 28 wt % Bis-GMA;
about 55 to about 70 wt %, based on the total dental restorative composition, of a filler system, wherein the filler system comprises a barium glass containing about 20 to about 60 wt % barium oxide based on the silanized barium glass;
an optional filler selected from the group consisting of fumed silica, colloidal silica, aluminosilicate glass, fluoroaluminosilicate glass, silica, quartz, strontium silicate, strontium borosilicate, lithium silicate, lithium alumina silicate, amorphous silica, ammoniated or deammoniated calcium phosphate, alumina, zirconia, tin oxide, titania, and combinations comprising at least one of the foregoing fillers; and
a curing system.

13. The composition of claim 12, wherein the optional filler is colloidal silica and comprises about 0 to about 4 wt % of the total dental restorative composition.

14. The composition of claim 12, wherein the barium glass comprises particles having an average particle size of about 0.3 to about 2 microns.

15. The composition of claim 12, wherein the dental restorative composition comprises a single flowable component, with a viscosity of about 200 Pa-s to about 800 Pa-s.

* * * * *